United States Patent
Smith et al.

(10) Patent No.: US 11,674,160 B2
(45) Date of Patent: Jun. 13, 2023

(54) MATERIALS AND METHODS FOR THE SYNTHESIS OF CARBON PRODUCTS FROM NON-BIOSYNTHETIC PROCESSES AND STREAMS

(71) Applicant: INV NYLON CHEMICALS AMERICAS, LLC, Wilmington, DE (US)

(72) Inventors: Gary Smith, Redcar (GB); Paul S. Pearlman, Redcar (GB); Gregory S. Kirby, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

(21) Appl. No.: 16/441,511

(22) Filed: Jun. 14, 2019

(65) Prior Publication Data

US 2019/0382804 A1 Dec. 19, 2019

Related U.S. Application Data

(60) Provisional application No. 62/686,807, filed on Jun. 19, 2018.

(51) Int. Cl.
*C12P 7/04* (2006.01)
*C12P 7/28* (2006.01)

(52) U.S. Cl.
CPC .. *C12P 7/04* (2013.01); *C12P 7/28* (2013.01)

(58) Field of Classification Search
None
See application file for complete search history.

(56) References Cited

U.S. PATENT DOCUMENTS

| | | | |
|---|---|---|---|
| 5,266,206 A * | 11/1993 | Baker | B01D 17/0208 210/640 |
| 9,663,801 B2 | 5/2017 | Pearlman et al. | |
| 9,777,295 B2 | 10/2017 | Botes et al. | |
| 9,862,973 B2 | 1/2018 | Botes et al. | |
| 9,920,339 B2 | 3/2018 | Botes et al. | |
| 10,167,487 B2 | 1/2019 | Conradie | |
| 10,252,183 B2 * | 4/2019 | Schultz | B01D 3/10 |
| 10,273,518 B2 | 4/2019 | Conradie et al. | |
| 10,294,496 B2 | 5/2019 | Botes et al. | |
| 2017/0145441 A1 | 5/2017 | Conradie et al. | |
| 2018/0094282 A1 | 4/2018 | Cartman et al. | C12P 5 007 |
| 2018/0100160 A1 | 4/2018 | Bawdon et al. | C12N 15 74 |
| 2019/0002926 A1 | 1/2019 | Cartman et al. | |
| 2019/0002927 A1 | 1/2019 | Foster et al. | C12P 5 007 |

FOREIGN PATENT DOCUMENTS

| | | |
|---|---|---|
| WO | 2017068385 A1 | 4/2017 |
| WO | 2018/064105 | 4/2018 |

OTHER PUBLICATIONS

Jingnan et al. (Studies on the production of branched-chain alcohols in engineered Ralstonia eutropha. Applied Microbiology and Biotechnology vol. 96, pp. 283-297 (2012)) (Year: 2012).*

Hua-Jiang Huang. A review of separation technologies in current and future biorefineries Separation and Purification Technology 62 (2008) 1-21 (Year: 2008).*

Berezina et al. "From organic pollutants to bioplastics: insights into the bioremediation of aromatic compounds by Cupriavidus necator" New Biotechnology 2015 32(1):47-53.

Byrd et al. "Bacterial Control of Agromyces ramosus in soil" Can J Microbiol 1985 31:1157-1163.

Chakravarty, J. & Brigham, C.J. "Solvent production by engineered Ralstonia eutropha: channeling carbon to biofuel" Applied Microbiology and Biotechnology 2018 102:5021-5031.

Grousseau et al. "Isopropranol production with engineered Cupriavidua necator as bioproduction platform" Appl. Microbiol. Biotechnol. 2014 98:4277-4290.

Kamilah et al. "Characteristics of used palm olein and its bioconversion into polyhydroxybutyrate by Cupriavidus necator H16" Malaysian Journal of Microbiology 2014 10(2) :139-148.

Koutinas et al. "Valorization of industrial waste and by-product streams via fermentation for the production of chemicals and biopolymers" Chem. Soc. Rev. 2014 43:2587.

Makkar, N.S. & Casida, L.E. "*Cupriavidus necator* gen. nov., sp. nov.: a Nonobligate Bacterial Predator of Bacteria in Soil" Int. J. of Systematic Bacteriology 1987 37(4) : 323-326.

Marc et al. "Over-expression of GroESL in Cupriavidus necator for heterotrophic and autotrophic isopropanol production" Metabolic Engineering 2017 42:74-84.

Raberg et al. "Ralstonia eutropha H16 in progress: Applications beside PHAs and establishment as production platform by advanced genertic tools" Critical reviews in Biotechnology 2018 38(4) :494-510.

Ramsay et al. "Use of a nylon manufacturing waste as an industrial fermentation substrate" Applied and Environmental Microbiology 1986 52(:1) 152-156.

Russell, J.B. "The energy spilling reactions of bacteria and other organisms" J Mol Microbiol Biotechnol. 2007 13(1-3):1-11.

Sillman, C. E. & Casida, L. E. "Isolation of nonobligate bacterial predators of bacteria from soil" Can J Microbiol 1986 32:760-762.

Schlegel, H.G. & Vollbrecht, D. "Formation of the Dehydroganses for Lactate, Ethanol and Butanediol in the Strictly Aerobi Bacterium Alcaligene eutrophus" Microbiology 1980 117:475-481.

Vlysidis et al. "A techno-economic analysis of biodiesel biorefineries: Assessment of integrated designs for the co-production of fuels and chemicals".

Vollbrecht and Schlegel "Excretion of Metabolites by Hydrogen Bacteria I. Autotrophic and Heterotrophic Fermentations" European Journal of Applied Microbiology and Biotechnology 1978 6(2) : 145-155.

(Continued)

*Primary Examiner* — Kagnew H Gebreyesus

(57) ABSTRACT

Methods, systems and compositions for producing at least one light-boiling, volatile, organic product using at least a portion of one or more carbon containing substances from a non-biosynthetic process in a biosynthetic process are provided. These methods, systems and compositions are useful in reducing waste treatment load of carbon containing chemical process waste streams.

18 Claims, 3 Drawing Sheets

Specification includes a Sequence Listing.

(56) References Cited

OTHER PUBLICATIONS

Vollbrecht and Schlegel "Excretion of Metabolites by Hydrogen Bacteria II. Influence of Aeration, pH, Temperature, and Age of Cells" European Journal of Applied Microbiology and Biotechnology 1978 6(2):157-166.

Vollbrecht and Schlegel "Excretion of Metabolites by Hydrogen Bacteria III. D(-)-3-hydroxybutenoate" European Journal of Applied Microbiology and Biotechnology 1979 7:259-266.

Vollbrecht and Schlegel "Excretion of Metabolites by Hydrogen Bacteria IV. Respiration Rate-Dependent Formation of Primary Metabolites and of Poly-3-hydroxybutanoate" European Journal of Applied Microbiology and Biotechnology 1979 7(3):267-276.

Zeph, L.E. & Casida, L.E. "Gram-negative versus gram-positive (actinomycete) nonobligate bacterial predators of bacteria in soil" Applied and Environmental Microbiology 1986 52(4):819-823

International Search Report and Written Opinion dated Sep. 30, 2019 in PCT/US2019/037157 filed Jun. 14, 2019.

International Search Report and Written Opinion dated Dec. 22, 2020 in PCT/US2019/037157 filed Jun. 14, 2019.

Grousseau, E., et al., "Isopropanol production with engineered Cupriavidus necatoras bioproduction platform", Applied Microbiology and Biotechnology, vol. 98, Issue 9, May 2014, pp. 4277-4290.

Koutinas, A.A., et al., "Valorization of industrial waste and by-product streams via fermentation for the production of chemicals and biopolymers", Chemical Society Reviews, vol. 43, Issue 8, Jan. 3, 2014, pp. 2587-2627.

Ramsay, B.A., et al., "Use of a Nylon Manufacturing Waste as an Industrial Fermentation Substrate", Applied and Environmental Microbiology, vol. 52, No. 1, Jul. 1986, pp. 152-156.

Vlysidis, A., et al., "A techno-economic analysis of biodiesel biorefineries: Assessment of integrated designs for the co-production of fuels and chemicals", Energy, vol. 36, Issue 8, 2011, pp. 4671-4683.

Steinbüchel et al., "Excretion of pyruvate by mutants of Alcaligenes eutrophus, which are impaired in the accumulation of poly(β-hydroxybutyric acid) (PHB), under conditions permitting synthesis of PHB", Applied Microbiology and Biotechnology, vol. 31, pp. 168-175, 1989.

* cited by examiner

OVERALL PROCESS CONCEPT

INTEGRATION WITH NON-BIO PROCESS

INTEGRATION WITH FINAL WASTE TREATMENT

MATERIALS AND METHODS FOR THE SYNTHESIS OF CARBON PRODUCTS FROM NON-BIOSYNTHETIC PROCESSES AND STREAMS

This patent application claims the benefit of priority from U.S. Provisional Application Ser. No. 62/686,807, filed Jun. 19, 2018, teachings of which are incorporated by reference in their entirety.

FIELD

The present invention teaches materials and methods for, inter alia, integrating one or more biosynthetic processes, including a fermentation process, and one or more non-biosynthetic processes, such as a chemical process, to utilize carbon in one or more carbon containing substances obtained from one or more waste streams of the non-biosynthetic process. An integrated system comprising a non-biosynthetic process and a biosynthetic fermentation process suitable for use with the present invention is included.

BACKGROUND

Various types of materials, including contaminated substances, can be treated through a process known as bioremediation. Bioremediation uses microorganisms to metabolize or break down a contaminated substance, by using the substance as a feedstock, thereby degrading the contaminated substance into a less harmful, less toxic or non-toxic substance. Composting and wastewater treatment facilities are long established microbiological processes for breaking down some substances.

In contrast to degrading such contaminated substances, there is some potential for utilizing substances comprising "waste" components, and/or by-products in streams from commercial and industrial sources, such as the food industry, pulp and paper industry, biodiesel and bioethanol production industries, in the production of chemicals and/or biopolymers using biosynthetic approaches (Koutinas, et al. Chem. Soc. Rev. 2014 43:2587). Koutinas et al. suggest that local or regional production of bio-based chemicals and materials could possibly be supported through the integration of new technologies in existing industrial plants where waste or by-product streams could be used as renewable feedstocks, suggesting the importance of downstream separation processes in such systems (Chem. Soc. Rev. 2014 43:2587). For example, the integration of a biodiesel refinery and fermentation process to produce succinic acid has been disclosed (Vlysidis et al. Energy 2011 36:4671-4683).

In a standard chemical process, a feedstock is added to the process and one or more chemical products are synthesized. Once the main product and any co-products have been synthesized, a "recovery" step allows certain elements to be recycled and to re-enter the chemical process. However, waste material from the chemical process must be disposed of in a waste treatment facility. For example, streams containing waste material produced from chemical processes are frequently burnt or disposed of in landfill sites, and a significant cost is typically associated with disposal of chemical process waste streams. An example is nonvolatile residue (NVR), which is a waste chemical stream from, for example, a cyclohexane oxidation process. NVR waste is typically disposed of in a landfill site or is burnt in purpose-built incinerators. Another example is sodium rich salt (SRS) streams, obtained from cyclohexane oxidation processes from a caprolactam and/or adipic acid manufacturing process. Such a waste stream needs to be disposed of in a landfill site because burning the SRS stream causes unwanted deposits in incinerators. Yet another example is purified terephthalic acid (PTA) waste residue obtained from a terephthalic acid process. PTA waste has been reported to be incinerated in a thermal oxidizer, but this waste stream is now in some instances reprocessed to recover chemical constituents such as organic, acids and metal elements.

The cost associated with disposal of chemical process waste streams suggests it would be desirable to deploy methods which reduce the waste treatment load of the waste streams from a chemical process to reduce the cost of disposing of these chemical process waste streams.

Ramsay et al. discloses use of NVR as a feedstock for certain industrial fermentation processes such as production of poly-β-hydroxybutyric acid and that NVR contains mainly small carboxylic acids, alcohols, aldehydes, esters and other organic compounds (Applied and Environmental Microbiology 1986 52(:1) 152-156). Ramsay, et al. report certain organisms, including *Ralstonia eutropha*, as suitable for metabolizing NVR components, utilizing them as a feedstock, in a limited number of industrial processes (Applied and Environmental Microbiology 1986 52(:1) 152-156).

The need exists for improved materials and methods of utilizing waste streams from non-biosynthetic, chemical processes in a biosynthetic fermentation process to produce one or more saleable products that are easy to separate from a fermentation broth while achieving acceptable productivity and capital cost (capital efficiency).

SUMMARY

The present invention provides materials and methods suitable for metabolizing carbon in a carbon containing substances obtained from a waste stream of a non-biosynthetic process, such as a fermentation process, to produce at least one light-boiling, volatile, organic compound which is saleable and easily separable from a fermentation broth. One aspect of the present invention relates to a reduced waste treatment load of a residual waste stream from a fermentation process as compared to the original waste stream(s) from the non-biosynthetic process.

Accordingly, an aspect of the present invention relates to a method for biosynthesizing a product from a carbon containing substance obtained from a waste stream of a non-biosynthetic process. The method comprises introducing the carbon containing substance to a biosynthetic fermentation process. An organism genetically modified to biosynthesize the product or increase biosynthesis of the product relative to that of a corresponding wild type organism is also added to the biosynthetic fermentation process. The added genetically modified organism is capable of utilizing carbon in the carbon containing substances and is selected from a species of *Cupriavidus* or *Ralstonia*, or an organism with properties similar thereto. The organism is then cultured under conditions suitable for biosynthesis of the product. Products produced in accordance with this method are light-boiling, volatile, organic compounds.

In one nonlimiting embodiment, the method provides a waste valorization process wherein the product is recovered as a valorized product or is used to generate heat and/or power.

In one nonlimiting embodiment, the method further comprises isolating and/or recovering the product via a process utilizing differences in volatility between the product and broth of the fermentation process.

In one nonlimiting embodiment, the product is isolated and/or recovered via distillation.

In one nonlimiting embodiment, the biosynthetic fermentation process is integrated with the non-biosynthetic process.

In one nonlimiting embodiment, the biosynthetic fermentation process is integrated with the non-biosynthetic process via heat and/or power generation.

In one nonlimiting embodiment, the biosynthetic fermentation process is provided as a pre-treatment stage with a waste treatment process.

In one nonlimiting embodiment, the biosynthetic fermentation process is provided as a pre-treatment stage with a waste treatment process via heat and/or power generation.

In one nonlimiting embodiment, the organism is genetically modified or physically adapted to have an improved ability to metabolize the carbon containing substance from the waste stream of the non-biosynthetic process and/or to have improved tolerance for growth in the waste stream.

In one nonlimiting embodiment, the organism has diminished polyhydroxyalkanoate synthesis.

Nonlimiting examples of waste streams from which the product may be derived include chemical processes selected from non-volatile residue (NVR) from a cyclohexane oxidation process, sodium-rich stream (SRS) from a cyclohexane oxidation process, purified terephthalic acid (PTA) residue from a terephthalic acid process, benzoic acid waste from a toluene oxidation process and isophthalic acid waste from a process of meta-xylene oxidation via oxygen.

Nonlimiting examples of carbon containing substances in the waste stream include aliphatic and aromatic carbon containing substances. Waste streams may further comprise inorganic compounds including metal-containing inorganic compounds.

In one nonlimiting embodiment, the carbon containing substance is at least one of a carboxylic acid, a dicarboxylic acid, a hydroxy acid, an aldehyde, an ester, an alcohol, a cresol, a nitrile or a corresponding salt or derivative related thereto.

In one nonlimiting embodiment, the method further comprises adding an auxiliary carbon source as a feedstock for the organism.

In one nonlimiting embodiment, the biosynthetic fermentation process is operated in continuous, batch, fed-batch or immobilised-bed mode.

In one nonlimiting embodiment, the biosynthetic fermentation process comprises nitrogen, phosphate and/or oxygen limitation.

Another aspect of the present invention relates to integrated systems comprising a non-biosynthetic process with a carbon containing substance derived from a waste stream, a biosynthetic fermentation process and an organism genetically modified to biosynthesize a product or increase biosynthesis of a product relative to that of a corresponding wild type organism.

Organisms useful in this integrated system are capable of utilizing carbon in the one or more carbon containing substances and are selected from a species of *Cupriavidus* or *Ralstonia*, or an organism with properties similar thereto.

Products produced with the system include light-boiling, volatile, organic compounds produced from the carbon containing substance derived from the waste stream of the non-biosynthetic process.

In one nonlimiting embodiment, the product produced via the integrated system is recovered as a valorized product or is used to generate heat and/or power.

In one nonlimiting embodiment, the fermentation process is integrated with the non-biosynthetic process.

In one nonlimiting embodiment, the fermentation process is integrated with the non-biosynthetic process via heat and/or power generation.

In one nonlimiting embodiment, the fermentation process is provided as a pre-treatment stage with a waste treatment process.

In one nonlimiting embodiment, the biosynthetic fermentation process is provided as a pre-treatment stage with a waste treatment process via heat and/or power generation.

Nonlimiting examples of waste streams from which the product may be derived include chemical processes selected from non-volatile residue (NVR) from a cyclohexane oxidation process, sodium-rich stream (SRS) from a cyclohexane oxidation process, purified terephthalic acid (PTA) residue from a terephthalic acid process, benzoic acid waste from a toluene oxidation process and isophthalic acid waste from a process of meta-xylene oxidation via oxygen.

Nonlimiting examples of carbon containing substances in the waste stream include aliphatic and aromatic carbon containing substances. Waste streams may further comprise inorganic compounds including metal-containing inorganic compounds.

In one nonlimiting embodiment, the carbon containing substance is at least one of a carboxylic acid, a dicarboxylic acid, a hydroxy acid, an aldehyde, an ester, an alcohol, a cresol, a nitrile or a corresponding salt or derivative related thereto.

Another aspect of the present invention relates to a composition contained in a bioreactor. The composition comprises an organism genetically modified to biosynthesize a product or increase biosynthesis of a product relative to that of a corresponding wild type organism, a carbon containing substance obtained from a waste stream of a non-biosynthetic process, and a fermentation-derived product from biosynthesis of the carbon containing substance obtained from the waste stream of the non-biosynthetic process by the organism. Organisms of the composition are capable of utilizing carbon in a carbon containing substances obtained from a waste stream of a non-biosynthetic process and are selected from a species of *Cupriavidus* or *Ralstonia*, or an organism with properties similar thereto. Fermentation-derived products of the composition include light-boiling, volatile, organic compounds.

Yet another aspect of the present invention relates to a process for producing isopropanol and/or acetone. The process comprises introducing a carbon containing substance obtained from a waste stream of a non-biosynthetic process to a biosynthetic fermentation process. An organism genetically modified to biosynthesize isopropanol and/or acetone or increase biosynthesis of isopropanol and/or acetone relative to that of a corresponding wild type organism is also added to the biosynthetic fermentation process. Organisms of the process are capable of utilizing carbon in the one or more carbon containing substances and are selected from a species of *Cupriavidus* or *Ralstonia*, or an organism with properties similar thereto. The method further comprises culturing the organism under conditions suitable for biosynthesis of the isopropanol and/or acetone so that isopropanol and/or acetone is produced.

In one nonlimiting embodiment, the organism is genetically modified to encode a polynucleotide with at least 50% sequence identity to SEQ ID NO: 1, 3, 5, 7 and/or 9 or a functional fragment thereof.

In one nonlimiting embodiment, the organism is genetically modified to comprise a polypeptide with at least 50% sequence identity to SEQ ID NO: 2, 4, 6, 8 and/or 10 or a functional fragment thereof.

DETAILED DESCRIPTION

Figure 1:
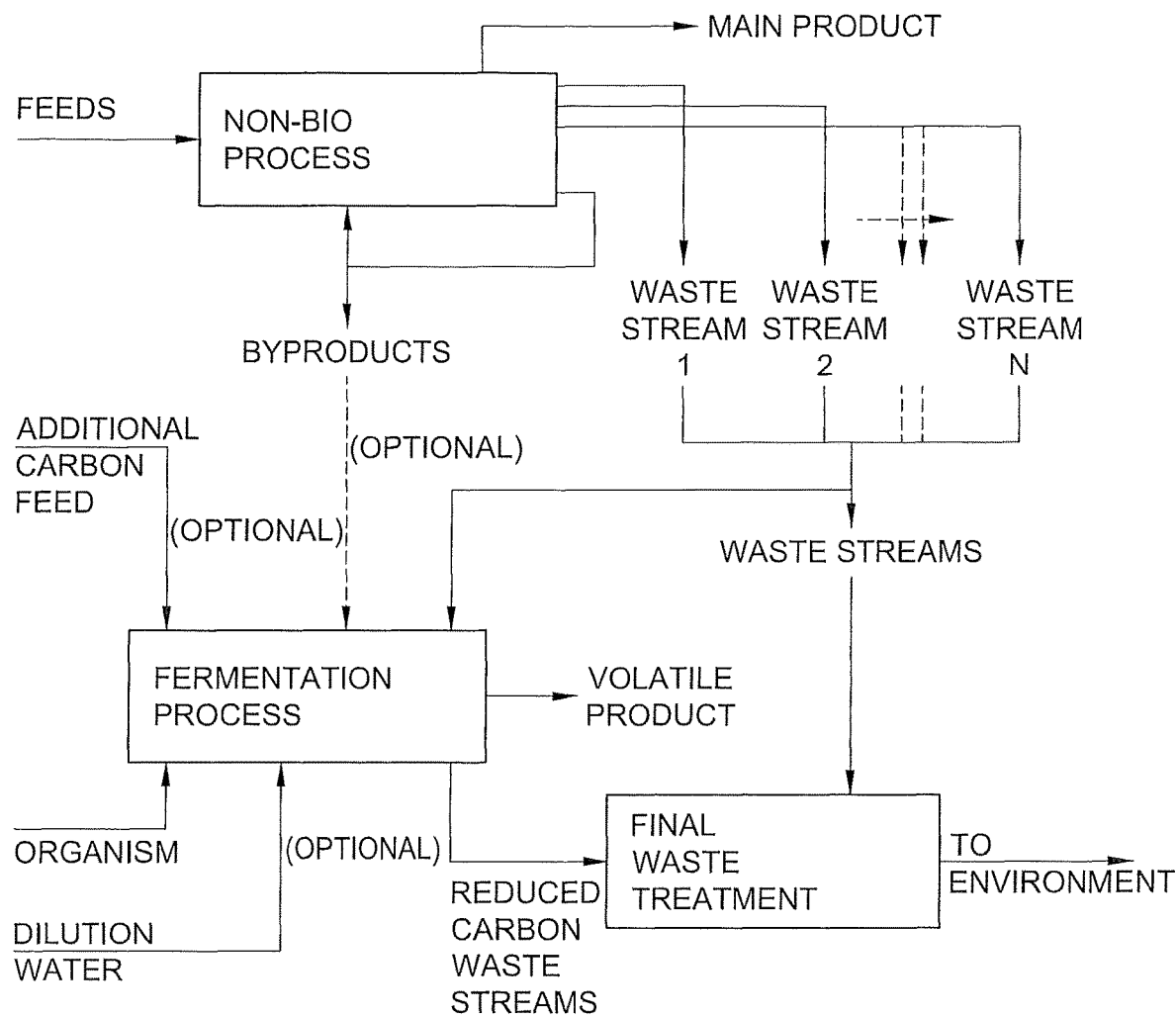
FIG. 1 provides a general summary of the stages of a chemical process.
Figure 2A:
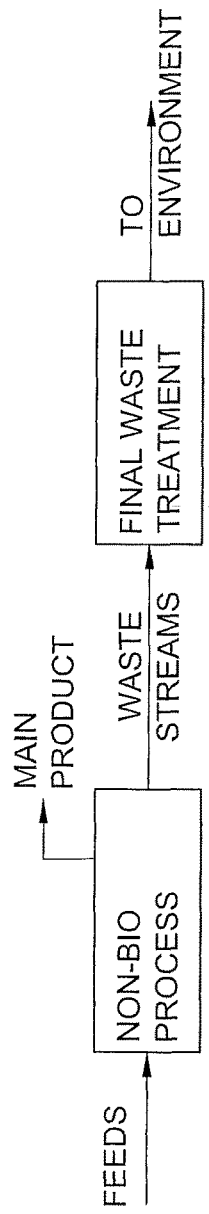
FIG. 2A provides a general summary of the stages of a chemical process.
Figure 2B:
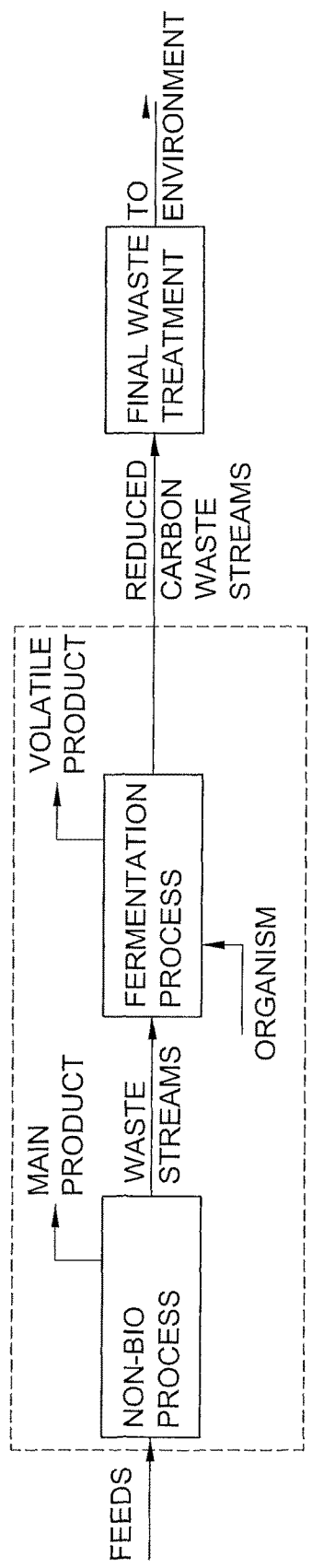
FIG. 2B provides a general summary of the stages of a chemical process integrated with a fermentation process in accordance with the present invention.
Figure 2C:
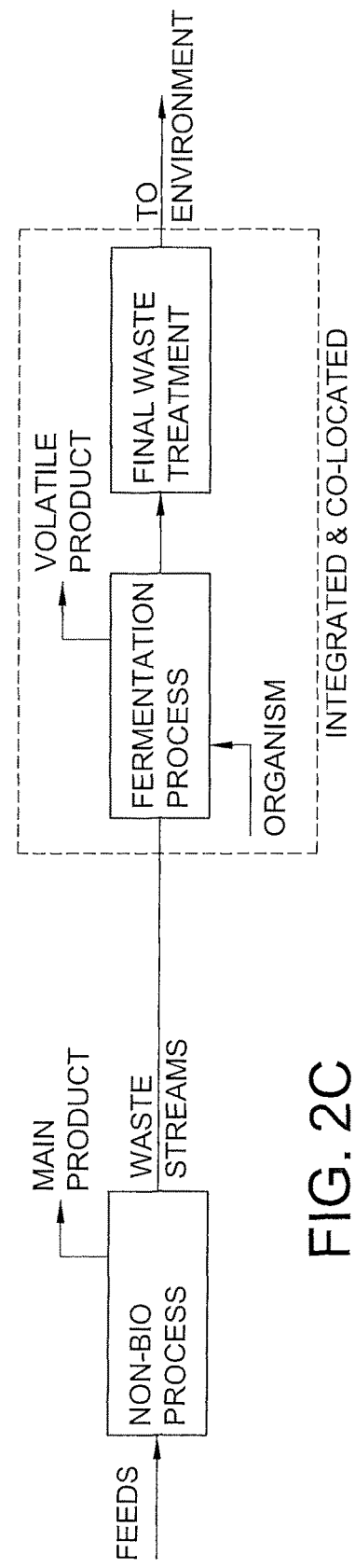
FIG. 2C provides a general summary of the stages of a chemical process integrated with a final waste treatment facility in accordance with the present invention.

The present invention provides methods for using one or more carbon containing substances obtained from one or more waste streams of a non-biosynthetic process as a feedstock in a fermentation process to produce a saleable and easily separable product. In a standard fermentation process, air, media, water and a feedstock are added to the fermentation process. The method of the present invention uses waste material, which may be from a chemical process, as the feedstock for the fermentation process. In the present invention, the saleable and easily separable product is a crude light-boiling volatile compound which is subsequently purified. Once this volatile product has been separated from the fermentation broth, the spent broth is subject to a step of water recovery wherein solids are removed to allow water to be recycled and used again in the fermentation process. Simultaneously, using these methods, the waste treatment load of the residual waste stream from the fermentation process is reduced compared to the original waste stream from the non-biosynthetic process.

For purposes of the present invention, when terms "a" or "an" are used herein to refer to a product, a waste stream, a carbon containing substance or an inorganic compound, they are meant to include one or more products, one or more waste streams, one or more carbon containing substances and/or one or more organic compounds.

The method of the present invention comprises adding one or more carbon containing substances obtained from one or more waste streams of a non-biosynthetic process to a fermentation process. In one nonlimiting embodiment, the non-biosynthetic process is a chemical process.

In one nonlimiting embodiment of the method of the present invention, wherein the carbon containing substance is in a chemical process waste stream, the entirety or at least a portion of the chemical process waste stream is fed to the fermentation process. Accordingly, the fermentation process can be constructed for any convenient scale including, but in no way limited to, production capacity and the appropriate portion of the chemical process waste stream required for that production capacity can be fed to the fermentation process. In embodiments of the present invention in which only at least a portion of the chemical process waste stream is fed to the fermentation process, the remainder of the chemical process waste stream continues to be fed to the conventional waste treatment system/waste disposal system but is a reduced load on that system compared to the original chemical process waste stream.

The one or more waste streams typically have low or no economic value, are unwanted, useless or inadequate and would otherwise be discarded. The one or more waste streams may comprise by-products or represent any unwanted stream from a non-biosynthetic process. The one or more waste streams are typically sent to waste disposal plants, such as landfill sites, deep well sites or purpose-built incinerators. The one or more waste streams may be used as a combined stream or may be used as individual waste streams in the biosynthetic fermentation process. The one or more waste streams are typically liquid.

The one or more waste streams may be from a non-biosynthetic process such as a chemical process selected from one of non-volatile residue (NVR) from a cyclohexane oxidation process, sodium-rich stream (SRS) from a cyclohexane oxidation process, purified terephthalic acid (PTA) residue from a terephthalic acid process, benzoic acid waste from a toluene oxidation process or isophthalic acid waste from a process of meta-xylene oxidation via oxygen.

The one or more waste streams may be from one non-biosynthetic process or may be mixed waste streams from more than one non-biosynthetic process. The one or more waste streams comprise one or more carbon containing substances. The one or more waste streams may also comprise one or more inorganic compounds. The inorganic compounds may include metals. During growth, the metals may be sequestered by the organism or may be immobilised in the biomass of the fermentation process.

The one or more carbon containing substances in the one or more waste streams are capable of being metabolized by an organism. In one non-limiting embodiment, the one or more carbon containing substances may be aliphatic or aromatic. The one or more carbon containing substances may be at least one of a carboxylic acid, a dicarboxylic acid, a hydroxy acid, an aldehyde, an ester, an alcohol, a cresol, a nitrile or a corresponding salt or derivative related thereto. In addition to the one or more carbon containing substances that are capable of being metabolized by an organism, one or more auxiliary carbon sources may be added to the biosynthetic fermentation process as a feedstock for the organism. In one non-limiting embodiment, the one or more auxiliary carbon sources may be fed to the biosynthetic fermentation process as a gaseous or liquid stream. In one non-limiting embodiment, the one or more auxiliary carbon sources may be gases such as carbon dioxide or hydrogen; sugars such as glucose, xylose or fructose; sugar acids such as gluconate; fatty acids or fats/oils, carboxylic acids such as propionic acid, lactic acid, and formic acid; amino acids, aromatics such as phenol and benzoic acid and/or alcohols such as glycerol.

For purposes of the present invention, by "derivatives and compounds related thereto" it is meant to encompass compounds derived from the same substrates and/or enzymatic reactions as these compounds, byproducts of these enzymatic reactions and compounds with similar chemical structure including, but not limited to, structural analogs wherein one or more substituents of the compounds are replaced with alternative substituents.

At least one of the organic compounds is fermentable. For example, in PTA, the main components are carboxylic acids and dicarboxylic acids; in NVR, the main components are fatty acids; and in SRS streams, the main components are short chain fatty acids. The stream may also contain inorganic salts, metal-containing-inorganic salts, halides and metals, for example, PTA wash effluent, in addition to carboxylic acids and dicarboxylic acid as well as cobalt, manganese, sodium and bromide.

The method further comprises adding an organism capable of metabolizing at least a portion of the carbon from the one or more carbon containing substances from the non-biosynthetic process to the fermentation process. The organism can be added before, during or after addition of the carbon containing substance. The organism can be added in an amount effective for the constructed fermentation process.

The organism added is an organism from a species of the *Cupriavidus* or *Ralstonia* genera or an organism with properties similar thereto that is capable of utilizing carbon in the one or more carbon containing substances. The organism is genetically modified to biosynthesize a product or increase biosynthesis of a product relative to that of a corresponding wild type organism. The product is a light-boiling, volatile, organic compound. In one nonlimiting embodiment, the organism is genetically modified by insertion of one or more exogenous genes to allow synthesis of a specific product.

The organism may be genetically modified or physically adapted to have an improved ability to metabolize the one or more carbon containing substances obtained from the one or more waste streams of the non-biosynthetic process and/or to have improved tolerance for growth in the one or more waste streams. In another nonlimiting embodiment, the organism may be genetically modified or otherwise adapted to make it better at utilizing the feedstock and/or growing in the feedstock. In one nonlimiting embodiment, the organism is genetically modified by insertion of one or more exogenous genes to allow synthesis of a specific product.

By "modification", "modifying" or "modify" for purposes of the present invention, it is meant that the gene is deleted, mutated, overexpressed or attenuated.

In certain aspects, the organism is modified by altering, engineering, or introducing one or more nucleic acid sequences within the organism. The altering or modifying of the nucleic acid sequences can be, for example and without limitation, via genetic engineering, by adaptive mutation, or by selective isolation of naturally occurring mutant strains.

In some nonlimiting embodiments, one or more enzymes or nucleic acids of the organism are modified via non-direct or rational enzyme design approaches with aims of improving activity, improving specificity, reducing feedback inhibition, reducing repression, improving enzyme solubility, changing stereo-specificity, or changing co-factor specificity. In some embodiments, the enzymes in the pathways outlined herein can be gene dosed (i.e., overexpressed by having a plurality of copies of the gene in the host organism), into the resulting genetically modified organism via episomal or chromosomal integration approaches. In some nonlimiting embodiments, genome-scale system biology techniques such as Flux Balance Analysis can be utilized to devise genome scale attenuation or knockout strategies for directing carbon flux. Attenuation strategies include, but are not limited to, the use of transposons, homologous recombination (double cross-over approach), mutagenesis, enzyme inhibitors, and RNA interference (RNAi). In some embodiments, fluxomic, metabolomic and transcriptomal data can be utilized to inform or support genome-scale system biology techniques, thereby devising genome-scale attenuation or knockout strategies in directing carbon flux. In some embodiments, the tolerance of the host microorganism to high concentrations of the extracellular product can be improved through continuous cultivation in a selective environment.

The modified nucleic acid sequences of the organism can include, for example, one or more enzymes, one or more promoters, one or more transcription factors, or combinations thereof. The modifications can be to nucleic acids encoding polypeptides or functional fragments thereof. The modifications can be to nucleic acids not directly involved in encoding polypeptides or functional fragments thereof, but indirectly affecting the polypeptides through the interconnected metabolic network and metabolic control strategy of the organism. The modification of the nucleic acid sequences can include one or more deletions, one or more substitutions, one or more insertions, or combinations thereof.

Enzymes with substitutions will generally have not more than 50 (e.g., not more than 1, not more than 2, not more than 3, not more than 4, not more than 5, not more than 6, not more than 7, not more than 8, not more than 9, not more than 10, not more than 12, not more than 15, not more than 20, not more than 25, not more than 30, not more than 35, not more than 40, or not more than 50) amino acid substitutions (e.g., conservative or non-conservative substitutions). This applies to any of the enzymes described herein and functional fragments thereof. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic, or acidic groups by another member of the same group can be deemed a conservative substitution. In contrast, a non-conservative substitution is a substitution of one amino acid for another with dissimilar characteristics. Deletion variants can, for example, lack 1, 2, 3, 4, 5, 6, 7, 8, 9, 10, 11, 12, 13, 14, 15, 16, 17, 18, 19, or 20 amino acid segments (of two or more amino acids) or non-contiguous single amino acids.

In one nonlimiting embodiment, modification of the organism is carried out by allele exchange. In this embodiment, genome edits are made in a *Cupriavidus* or *Ralstonia* organism with perturbed PHB synthesis or an organism with properties similar thereto by allele exchange (also referred to as allelic exchange). In one non-limiting embodiment, the organism is a ΔphaCAB H16 *C. necator* strain generated using allele exchange.

The term 'allele' is often used interchangeably with the term 'gene' more generally, and refers to a defined genomic locus. In allele exchange, a specific run of DNA sequence (i.e., the native allele) in a genome of an organism is literally exchanged for a recombinant, mutant, or synthetic run of DNA sequence (i.e., the recombinant allele). Depending on the nature of the recombinant allele, this allele exchange can result in a gene deletion, a gene substitution, or a gene insertion.

In one nonlimiting embodiment, recombinant/synthetic alleles can be constructed via gene synthesis and/or standard molecular biology techniques. These alleles are then cloned into a plasmid vector for transfer into the organism and execution of the allele exchange procedure.

In some nonlimiting embodiments, the organism is modified to include one or more exogenous nucleic acid sequences.

The term "exogenous" as used herein with reference to a nucleic acid (or a protein) and an organism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In some nonlimiting embodiments, the organism is capable of metabolizing more than one organic compound in the carbon containing substance. In one nonlimiting embodiment, the organism is capable of utilizing carbon from more than one carbon containing substance.

In one nonlimiting embodiment, the organism tolerates compounds or components which are toxic to traditional organisms used for producing products such as *E. coli*, *Yarrowia* and yeast and can grow in waste streams from non-biosynthetic processes such as chemical process waste streams and the conditions of those streams. In one nonlimiting embodiment, the organism is a microorganism selected from non-pathogenic members of the genera *Cupriavidus* or *Ralstonia*. Nonlimiting examples of species of *Cupriavidus* or *Ralstonia* useful in accordance with this disclosure include *Cupriavidus necator*, *Cupriavidus metallidurans*, *Cupriavidus taiwanensis*, *Cupriavidus pinatubonensis*, *Cupriavidus basilensis* and *Ralstonia pickettii*. In one nonlimiting embodiment, the microorganism is *Cupriavidus necator* (*C. necator*), previously also referred to as *Hydrogenomonas eutrophus*, *Alcaligenes eutropha*, *Ralstonia eutropha*, and *Wautersia eutropha*, which is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar and Casida; 1987), bacterial predation (Byrd et al., 1985; Sillman & Casida, 1986; Zeph & Casida, 1986) and polyhydroxybutyrate (PHB) synthesis. In addition, the cells have been reported to be capable of both aerobic or nitrate dependent anaerobic growth.

By "an organism with properties similar thereto" it is meant an organism having one or more of the above-mentioned properties of *C. necator*.

A nonlimiting example of a *C. necator* organism useful in the present invention is a *C. necator* of the H16 strain. In one nonlimiting embodiment, a *C. necator* host of the H16 strain with at least a portion of the phaC1AB1 gene locus knocked out (ΔphaCAB), as described in U.S. patent application Ser. No. 15/717,216, teachings of which are incorporated herein by reference, is used.

In one nonlimiting embodiment, a *C. necator* host of the H16 strain may be further modified to eliminate the A0006-9 operon encoding endonucleases thereby improving transformation efficiency as described in U.S. patent application Ser. No. 15/717,216, teachings of which are incorporated herein by reference.

In one embodiment, the organism has diminished polyhydroxyalkanoate (PHA) synthesis. The diminished polyhydroxyalkanoate (PHA) synthesis may be diminished polyhydroxybutyrate (PHB) synthesis. The natural mechanism of PHB synthesis is detrimental to obtaining high productivity and/or product yields. Attenuation or elimination of PHA synthesis is therefore required in order to maximize the efficiency of generating the desired product.

For purposes of the present invention, by "diminishing" or "diminished" polyhydroxybutyrate synthesis, it is meant that the organism is altered to synthesize less polyhydroxybutyrate as compared to an unaltered wild-type organism of the same species. Organisms used in this disclosure can exhibit at least 20%, 25%, 30%, 40%, 50% or even greater decreased polyhydroxybutyrate synthesis as compared to an unperturbed wild-type organism of the same species.

In one nonlimiting embodiment, the organism is genetically modified to synthesize isopropanol and/or acetone and encodes a polynucleotide selected from SEQ ID NO: 1, 3, 5, 7 and/or 9 or a functional fragment thereof or a polynucleotide with at least 50%, 60%, 70%, 75%, 80%, 85%, 90%, 95% or 99% sequence identity to SEQ ID NO: 1, 3, 5, 7 and/or 9 or a functional fragment thereof. In one nonlimiting embodiment, the polynucleotide is codon optimized for expression in *C. necator*.

In one nonlimiting embodiment, the organism is genetically modified to synthesize isopropanol and/or acetone and comprises a polypeptide selected from SEQ ID NO: 2, 4, 6, 8 and/or 10 or a functional fragment thereof or a polypeptide with at least 50%, 60%, 70%, 75%, 80%, 85%, 90%, 95% or 99% sequence identity to SEQ ID NO: 2, 4, 6, 8 or 10 and/or a functional fragment thereof.

The percent identity (homology) between two amino acid sequences as disclosed herein can be determined as follows. First, the amino acid sequences are aligned using the BLAST 2 Sequences (Bl2seq) program from the stand-alone version of BLAST containing BLASTP version 2.9.0. This stand-alone version of BLAST can be obtained from the U.S. government's National Center for Biotechnology Information web site (www with the extension ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be followed for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the polypeptides or nucleic acid sequences described herein can also be used in the methods and organisms disclosed herein. The term "functional fragment" as used herein refers to a peptide fragment of a polypeptide or a nucleic acid sequence fragment encoding a peptide fragment of a polypeptide that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, polypeptide. The functional fragment can generally, but not always, be comprised of a continuous region of the polypeptide, wherein the region has functional activity.

The organism is then cultured under conditions suitable for biosynthesis of one or more light-boiling, volatile, organic compounds.

The biosynthetic fermentation process may be operated in any of the following modes; continuous, batch, fed-batch or immobilized-bed mode. The specific operating conditions of these different modes would be within the knowledge of the skilled artisan.

Under conditions of nutrient limitation a phenomenon known as overflow metabolism (also known as energy spilling, uncoupling or spillage) occurs in many bacteria (Russell, 2007). In growth conditions in which there is a relative excess of carbon source and other nutrients (e.g. phosphorous, nitrogen and/or oxygen) are limiting cell growth, overflow metabolism results in the use of this excess energy (or carbon), not for biomass formation but for the excretion of metabolites, typically organic acids. In *C. necator* a modified form of overflow metabolism occurs in which excess carbon is sunk intracellularly into the storage carbohydrate polyhydroxybutyrate (PHB). In strains of *C. necator* which are deficient in PHB synthesis this overflow metabolism can result in the production of extracellular overflow metabolites. The range of metabolites that have been detected in PHB deficient *C. necator* strains include acetate, acetone, butanoate, cis-aconitate, citrate, ethanol, fumarate, 3-hydroxybutanoate, propan-2-ol, malate, methanol, 2-methyl-propanoate, 2-methyl-butanoate, 3-methyl-butanoate, 2-oxoglutarate, meso-2,3-butanediol, acetoin, DL-2,3-butanediol, 2-methylpropan-1-ol, propan-1-ol, lactate 2-oxo-3-methylbutanoate, 2-oxo-3-methylpentanoate, propanoate, succinate, formic acid and pyruvate. The range of overflow metabolites produced in a particular fermentation can depend upon the limitation applied (e.g. nitrogen, phosphate, oxygen, carbon), the extent of the limitation, and the carbon source provided (Schlegel and Vollbrecht, 1980; Steinbuchel and Schlegel, 1989; Vollbrecht et al., 1978 and 1979; Vollbrecht and Schlegel, 1978 and 1979). Applying a suitable nutrient limitation in defined fermentation conditions can thus result in an increase in the flux through a particular metabolic node. The application of this knowledge to *C. necator* strains genetically modified to produce desired chemical products via the same metabolic node can result in increased production of the desired product.

In the biosynthetic fermentation process described herein, a fermentation strategy can be used that entails anaerobic, micro-aerobic or aerobic cultivation coupled with nutrient limitation such as nitrogen, oxygen or phosphorus limitations or gradients thereof and any combinations thereof.

In a non-limiting example, a cell retention strategy using a ceramic hollow fiber membrane can be employed to achieve and maintain a high cell density during fermentation.

Organisms grow under various engineering and physical conditions inside the fermenter such as agitation, mixing, aeration, pressure, shear, temperature and pH. The pH in the fermentation process according to the present invention is maintained in a pH range that is suitable for the organism of the fermentation process such as, but not limited to, from 4 to 9 pH, or such as 5.5 to 7.5 pH, by adjusting the pH of the chemical process waste stream, or by adjusting the pH of the fermentation broth in the fermentation process, or by a combination thereof.

The total solute (i.e., total solids) concentration of the broth in the fermentation process is maintained in a range from 5 to 15 wt %. In one nonlimiting embodiment, the total solute concentration is 10 wt %. If the total solute concentration in the carbon containing substance from the non-biosynthetic process is higher, it can be diluted with water to achieve an acceptable total solute concentration that can be tolerated by the organism. This dilution may be accomplished prior to the carbon containing substance from the non-biosynthetic process being fed to the fermentation process or may occur within the fermentation process as a result of the feed rate of the carbon containing substance from the non-biosynthetic process being small in comparison to the total dilution rate in the fermentation due to media feed. Use of a fed-batch fermentation process can increase the ease of maintaining a constant concentration of organic compounds within the desired range.

The concentration of organic compounds in the carbon containing substance from the non-biosynthetic process must be at least 1 wt %. If the concentration of organic compounds in the carbon containing substance from the non-biosynthetic process is too high, it may be diluted with water to achieve an acceptable organic compounds concentration that can be tolerated by the organism. This dilution may be accomplished prior to the carbon containing substance from the non-biosynthetic process being fed to the fermentation process or may occur within the fermentation process as a result of the feed rate of the carbon containing substance from the non-biosynthetic process being small in comparison to the total dilution rate in the fermentation due to media feed. Use of a fed-batch fermentation process can increase the ease of maintaining a constant concentration of organic compounds within the desired range.

In one nonlimiting embodiment, the product of the fermentation process is a light-boiling, volatile organic compound.

For purposes of the present invention, the product definition of "light-boiling, volatile, organic compound" is meant to encompass any organic compound of carbon or its azeotrope and other metabolites within the fermentation broth having a lower boiling point temperature than water at the normal operating pressure of the bioremediation process, such that the product can easily be separated from the fermentation broth by flash separation, evaporation, distillation, and other separation techniques utilizing difference in volatility between the product and fermentation broth that would be well known to a person skilled in the art. Such separation techniques using difference in volatility between the product and fermentation broth allow separation based on the lower volatility of the product. In one nonlimiting embodiment, the product may be a liquid or its azeotrope such as one of isopropanol, acetone, isoprene, ethanol, n-propanol, acetaldehyde or ethyl acetate. In one nonlimiting embodiment, the product may be a gas such as one of isobutylene and butadiene. For the avoidance of doubt, the product definition excludes carbon monoxide, carbon dioxide, carbonic acid, metallic carbides or carbonates and ammonium carbonate. In one nonlimiting embodiment, the product is recovered as a valorized product or is used to generate heat and/or power.

Nonlimiting methods for biosynthesis of various light-boiling, volatile, organic compounds and nonlimiting examples of genetically modified organisms for use in biosynthetic production methods for such compounds are set forth in U.S. Pat. Nos. 10,294,496; 9,663,801; 9,920,339; 10,273,518; 9,862,973; 10,167,487; and 9,777,295 as well as U.S. patent application Ser. Nos. 15/238,225; 15/717,065; 16/023,055; and Ser. No. 16/022,878, teachings of which are herein incorporated by reference in their entireties.

By valorized production it is a meant a product obtained via a waste valorization process of reusing, recycling or composting waste materials and converting them into more useful products including materials, chemicals, fuels or other sources of energy. "Waste-to-energy" aspects are becoming more prominent due to the rapid depletion of natural resources and increase in waste generation. See the website of the American Institute of Chemical Engineers (AIChE) at aiche with the extension .org/cei/topics/energy/waste-valorization of the world wide web.

In a non-limiting example, co-products may accompany the formation of the product. Such co-products of the fermentation process may include carbon dioxide (in an offgas stream) and biomass (in a bleed stream). The carbon dioxide may be suitable for use as a carbon feed source for another chemical or bio-process. In a non-limiting example, the biomass may be deactivated, concentrated to a thick solids stream, and fed to a solid waste disposal process.

The methods of the present invention may further comprise recovering produced product from the organism. Once produced, any method can be used to isolate these products or derivatives or compounds related thereto.

The isolation of one or more products can involve any one or more downstream processes generally known to be suitable for the at least partial separation and/or isolation of material from a reaction or biosynthetic fermentation process. The collection can, for example, involve centrifugations, cell disruptions, concentrations, precipitations, extractions, filtrations, crystallizations, distillations, chemical conversions, or combinations thereof. One or more biosynthetic products can be collected from the liquid or solid phase of the culture, or from the gas phase present in the headspace of a bioreactor or the off-gas.

In one non-limiting embodiment, the biosynthetic fermentation process is integrated either with the non-biosynthetic process or as a pre-treatment stage with a waste treatment process. Integration of the biosynthetic fermentation process with the non-biosynthetic process allows for biosynthesis of a valorized product from one or more waste streams from the non-biosynthetic process. Further, the integration of the biosynthetic fermentation process with the non-biosynthetic process obviates the requirement to transport the one or more waste streams from the non-biosynthetic process to the biosynthetic fermentation process. Integration of the biosynthetic fermentation process as a pre-treatment stage with a waste treatment process allows biosynthesis of a valorized product before the one or more waste streams pass to a final waste treatment process. Advantageously, this reduces the load for the final waste treatment process, thereby lowering costs and use of resources.

In an alternative embodiment, the biosynthetic fermentation process is integrated either with the non-biosynthetic process or as a pre-treatment stage with a waste treatment process via heat and/or power generation.

In one non-limiting embodiment, the biosynthetic fermentation process is physically integrated either with the non-biosynthetic process or as a pre-treatment stage with a waste treatment process.

Thus, the present invention also provides integrated systems comprising a non-biosynthetic process and a fermentation process for biosynthesizing a product from one or more carbon containing substances obtained from the non-biosynthetic process. In one nonlimiting embodiment, the fermentation process is integrated with the non-biosynthetic process. In one nonlimiting embodiment, the fermentation process is integrated with the non-biosynthetic process via heat and/or power generation. In nonlimiting embodiments wherein the non-biosynthetic process is a chemical process, integration of the fermentation process to metabolize the chemical waste stream can result in both production of valuable products and a reduction in the total load of the waste stream.

Also provided by the present invention are compositions contained in a bioreactor comprising an organism selected from a species of *Cupriavidus* or *Ralstonia*, or an organism with properties similar thereto, capable of utilizing carbon in one or more carbon containing substances obtained from one or more waste streams of a non-biosynthetic process and genetically modified to biosynthesize a product or increase biosynthesis of a product relative to that of a corresponding wild type organism, as described herein, one or more carbon containing substances obtained from one or more waste streams of a non-biosynthetic process and a fermentation-derived product from biosynthesis of the one or more carbon containing substances obtained from the one or more waste streams of the non-biosynthetic process by the organism. The product is a light-boiling, volatile, organic compound.

Further, the present invention provides bio-derived, bio-based, and fermentation-derived products produced from any of the methods, organisms, systems and compositions described herein. In one nonlimiting embodiment, the products may be compositions comprising at least one bio-derived, bio-based, or fermentation-derived compound or any combination thereof. In one nonlimiting embodiment, the products may be bio-derived, bio-based, or fermentation-derived polymers comprising the bio-derived, bio-based, or fermentation-derived composition or compound, or any combination thereof. In one nonlimiting embodiment, the product may be a bio-derived, bio-based, or fermentation-derived cis-polyisoprene rubber, trans-polyisoprene rubber, or liquid polyisoprene rubber, comprising the bio-derived, bio-based, or fermentation-derived compound or bio-derived, bio-based, or fermentation-derived composition, or any combination thereof or the bio-derived, bio-based, or fermentation-derived polymer, or any combination thereof. In one nonlimiting embodiment, the product may be a molded substance obtained by molding the bio-derived, bio-based, or fermentation-derived polymer, or the bio-derived, bio-based, or fermentation-derived rubber, or any combination thereof. In one nonlimiting embodiment, the product may be a bio-derived, bio-based, or fermentation-derived formulation comprising the bio-derived, bio-based, or fermentation-derived composition or compound, the bio-derived, bio-based, or fermentation-derived polymer, the bio-derived, bio-based, or fermentation-derived rubber, or the bio-derived, bio-based, or fermentation-derived molded substance, or any combination thereof. In one nonlimiting embodiment, the product may be a bio-derived, bio-based, or fermentation-derived semi-solid or a non-semi-solid stream, comprising the bio-derived, bio-based, or fermentation-derived composition or compound, the bio-derived, bio-based, or fermentation-derived polymer, the bio-derived, bio-based, or fermentation-derived rubber, the bio-derived, bio-based, or fermentation-derived formulation, or the bio-derived, bio-based, or fermentation-derived molded substance, or any combination thereof.

The following section provides further illustration of the methods and compositions of the present invention. These working examples are illustrative only and are not intended to limit the scope of the invention in any way.

EXAMPLES

Example 1: Making Isopropanol (IPA) Using Waste SRS from a Chemical Process as a Feedstock Sodium-rich streams (SRS) originate from cyclohexane oxidation in caprolactam and/or adipic acid processes. These waste streams are disposed of in landfill sites or are burnt in purpose-built incinerators, incurring an unwanted cost associated with the chemical process. This example describes the re-use of SRS waste streams to make isopropanol (IPA/$C_3H_8O$), and also acetone.

Isopropanol is a volatile, saleable product with many uses, including as a solvent in a variety of industries such as, but not limited to, paint stripping and extraction of laboratory chemicals, as a surface disinfectant such as used in for example, but not limited to hospitals and laboratories, as an antiseptic as used, for example, but not limited to, in hand sanitizers, as a sample preservative, and manufacturing processes to make, for example, but not limited to, acetone, glycerol and isopropyl acetate.

Preparation of SRS Feedstock Medium

SRS comprises of a variety of organic acid salts with various carbon chain lengths ($C_1$-$C_6$) up to 100 g/L in concentration. These serve as the sole form of organic carbon in SRS feedstock medium, which was prepared in a concentrated form and diluted to a working concentration using autoclaved, distilled water and a 2× concentrated, filter-sterilized minimal medium (comprising nitrogen, phosphate and trace element sources as required).

Strain Preparation

The strain *Cupriavidus necator* H16 was modified to eliminate phaCAB, involved in polyhydroxyisobutyrate (PHB) production and A0006-9 encoding endonucleases thereby improving transformation efficiency as described in U.S. patent application Ser. No. 15/717,216, teachings of which are incorporated herein by reference.

Plasmid Preparation

An expression vector harbouring 5 genes was constructed using standard cloning techniques. Table 1 shows the genes used in assembly of the construct whilst Table 2 shows the polypeptide functions. The nucleotide and amino acid sequences of the five genes used are provided in the APPENDIX as SEQ ID NO: 1 to SEQ ID NO: 10.

TABLE 1

| SEQ ID NO | Gene name | Host of origin | Codon optimized for *C. necator* |
|---|---|---|---|
| 1 | H16_A1445 | *Cupriavidus necator* | no |
| 3 | H16_A1331 | *Cupriavidus necator* | no |
| 5 | H16_A1332 | *Cupriavidus necator* | no |
| 7 | 824 CA_P1065* | *Clostridium acetobutylicum* | yes |
| 9 | CbeAF157307* | *Clostridium beijerinkii* | yes |

*Genes 824 CA_P1065 and CbeAF157307 were taken from Grousseau, E., Lu, J., Gorret, N. et al. Appl Microbiol Biotechnol (2014) 98: 4277.

TABLE 2

| SEQ ID NO: | Description | Unitprot Identifier |
|---|---|---|
| 2 | beta-ketothiolase, BktB, EC 2.3.1.16, EC 2.3.1.9 | Q0KBP1 |
| 4 | Succinyl-CoA: 3-ketoacid-coenzyme A transferase subunit A, EC 2.8.3.5 | Q0KC00 |
| 6 | Succinyl-CoA: 3-ketoacid-coenzyme A transferase subunit B, EC 2.8.3.5 | Q0KBZ9 |
| 8 | acetoacetate decarboxylase | P23670 |
| 10 | alcohol dehydrogenase | P25944 |

Preparation of Cell Culture for Isopropanol (IPA) Production Experiments

Precultures of both an IPA pathway expressing strain and empty vector control strain were prepared in a selective, fructose based minimal medium. The cultures were incubated at 30° C. with shaking, for up to 36 hours and washed prior to subsequent use.

Seed Cultures for Inoculation of Fermenters

Washed cell suspensions were transferred to a SRS based selective minimal media, incubated overnight and then sub-cultured to the same media and further incubated for 16 hours. These were used as a direct inoculum for the fermentation. The seed cultures for the fructose based fermentations (controls, see next section) were prepared in exactly the same way but in a fructose based media.

Fermentation Conditions

A Sartorius Ambr15f platform was used to screen pathway strains in a batch mode of operation. Both the IPA expressing strain and equivalent empty vector controls, were run on both fructose (controls and SRS based media. All fermentations were run in batch mode, at 30° C., and with sufficient aeration and agitation to meet a minimal dissolved oxygen demand of 10% vv. The fermentation process was run for 48 hours, at which time point samples were taken.

Sample Preparation for Analysis

Figure 3:
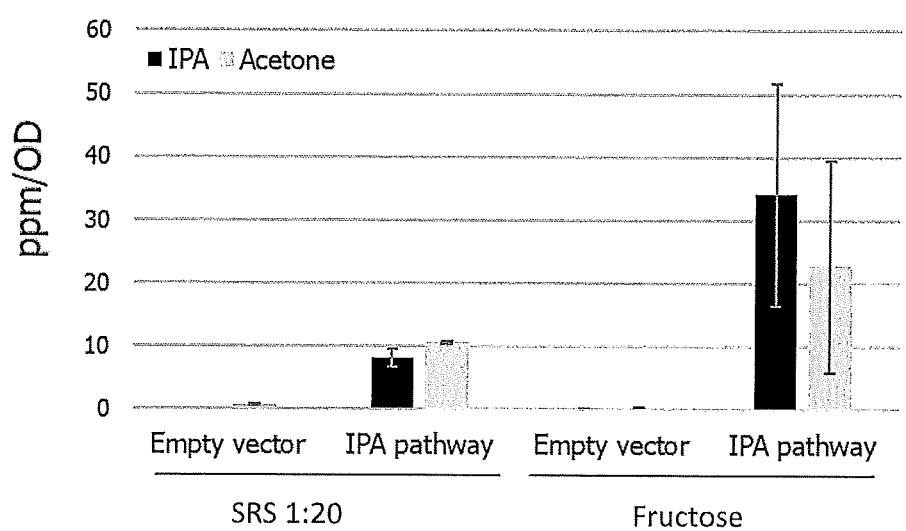
FIG. 3 shows isopropanol and acetone production in SRS or 1% fructose supporting growth of the IPA pathway containing strain and empty vector control strain, respectively. Error bars represent 2 standard deviations of triplicate repeats for each condition.

Samples volumes were usually 1 ml. Optical density measurements were taken and then they were centrifuged for 20 minutes at 4000 rpm. The clarified supernatants were then subject to analysis of the IPA and acetone by GC-MS. A sample was taken at a 48-hour time point from the biosynthetic fermentation process and data are shown in FIG. 3. The results show that the strain of *Cupriavidus necator* used within this Example was able to produce isopropanol (and acetone) using waste SRS from a chemical process. In the Ambr-15f, an average of 60.5 ppm IPA and 78.7 ppm acetone was produced (139.2 ppm combined), compared to 475 ppm IPA and 317 ppm acetone from fructose (792 ppm combined; FIG. 3). When data were normalized to $OD_{600}$ biomass readings, it was concluded that utilization of fructose as the sole carbon source delivered approximately 5.7-fold more product than SRS, despite the total available carbon in both samples being roughly equivalent (0.33% for SRS 1:20 and 0.4% in the case of 1% fructose). The lower overall IPA and acetone yield in SRS compared to fructose can be partly explained by the expected theoretical yield on both substrates. It is noteworthy that the conversion of fructose to IPA is theoretically on a mole-to-mole basis (i.e. one mole of fructose produces one mole of acetyl-coA which in turn produces one mole of IPA (or acetone)). In contrast, SRS yielded comparatively less IPA/acetone.

What is claimed is:

1. A method for biosynthesizing a product from a carbon containing substance obtained from a waste stream of a non-biosynthetic process, comprising:
(a) introducing the carbon containing substance obtained from the waste stream of the non-biosynthetic process to a biosynthetic fermentation process;
adding to the biosynthetic fermentation process a *Cupriavidus* necator host of the H16 strain with at least a portion of the phaC1AB1 gene locus knocked out (ΔphaCAB) and genetically modified to comprise polynucleotides with at least 90% sequence identity to SEQ ID NO: 1, 3, 5, 7 and 9 or encode polypeptides with at least 90% sequence identity to SEQ ID NO: 2, 4, 6, 8 and 10 which exhibit at least 75% of the activity of the corresponding mature, full-length, polypeptide of SEQ ID NO:2, 4, 6, 8 and 10;
(b) culturing the organism under conditions suitable for biosynthesis of the product;
(c) biosynthesizing the product, wherein the product is selected from the group consisting of isopropanol, acetone, isoprene, ethanol, n-propanol, acetaldehyde, ethyl acetate, isobutylene and butadiene; and
(d) isolating and/or recovering the product via a process utilizing differences in volatility between the product and broth of the fermentation process.

2. The method of claim 1, wherein the method is a waste valorization process, and wherein the product is recovered as a valorized product or is used to generate heat and/or power.

3. The method of claim 1, wherein the biosynthetic fermentation process is integrated either with the non-biosynthetic process or as a pre-treatment stage with a waste treatment process.

4. The method of claim 3, wherein the biosynthetic fermentation process is integrated either with the non-biosynthetic process or as a pre-treatment stage with a waste treatment process via heat and/or power generation.

5. The method of claim 1, wherein the organism is genetically modified or physically adapted to have an improved ability to metabolize the carbon containing substance from the waste stream of the non-biosynthetic process and/or to have improved tolerance for growth in the waste stream.

6. The method of claim 1, wherein the organism has diminished polyhydroxyalkanoate synthesis.

7. The method of claim 1, wherein the carbon containing substance is aliphatic or aromatic.

8. The method of claim 1 wherein the carbon containing substance is at least one of a carboxylic acid, a dicarboxylic acid, a hydroxy acid, an aldehyde, an ester, an alcohol, a cresol, a nitrile or a corresponding salt or derivative related thereto.

9. The method of claim 1, further comprising the step of adding an auxiliary carbon source as a feedstock for the organism.

10. The method of claim 1, wherein the biosynthetic fermentation process comprises nitrogen, phosphate and/or oxygen limitation.

11. An integrated system comprising:
a non-biosynthetic process with one or more carbon containing substances derived from a waste stream, wherein the carbon containing substance is at least one of a carboxylic acid, a dicarboxylic acid, a hydroxy acid, an aldehyde, an ester, an alcohol, a cresol, a nitrile or a corresponding salt or derivative related thereto;
a biosynthetic fermentation process; and
a Cupriavidus necator host of the H16 strain with at least a portion of the phaC1AB1 gene locus knocked out (ΔphaCAB) and genetically modified to comprise polynucleotides with at least 90% sequence identity to SEQ ID NO: 1, 3, 5, 7 and 9 or encode polypeptides with at least 90% sequence identity to SEQ ID NO: 2, 4, 6, 8 and 10 which exhibit at least 75% of the activity of the corresponding mature, full-length, polypeptide of SEQ ID NO:2, 4, 6, 8 and 10,
wherein the organism is capable of utilizing carbon in the one or more carbon containing substances, and
wherein the product is selected from the group consisting of isopropanol, acetone, isoprene, ethanol, n-propanol, acetaldehyde, ethyl acetate, isobutylene and butadiene and produced from the carbon containing substance derived from the waste stream of the non-biosynthetic process.

12. The integrated system of claim 11, wherein the product is recovered as a valorized product or is used to generate heat and/or power.

13. The integrated system of claim 11, wherein the fermentation process is integrated either with the non-biosynthetic process or as a pre-treatment stage with a waste treatment process.

14. The integrated system of claim 13, wherein the fermentation process is integrated either with the non-biosynthetic process or as a pre-treatment stage with a waste treatment process via heat and/or power generation.

15. The integrated system of claim 11, wherein the carbon containing substance is aliphatic or aromatic.

16. A composition contained in a bioreactor comprising:
a Cupriavidus necator host of the H16 strain with at least a portion of the phaC1AB1 gene locus knocked out (ΔphaCAB) and genetically modified to comprise polynucleotides with at least 90% sequence identity to SEQ ID NO: 1, 3, 5, 7 and 9 or encode polypeptides with at least 90% sequence identity to SEQ ID NO: 2, 4, 6, 8 and 10 which exhibit at least 75% of the activity of the corresponding mature, full-length, polypeptide of SEQ ID NO:2, 4, 6, 8 and 10,
wherein the organism is capable of utilizing carbon in a carbon containing substance obtained from a waste stream of a non-biosynthetic process
a carbon containing substance obtained from a waste stream of a non-biosynthetic process, wherein the carbon containing substance is at least one of a carboxylic acid, a dicarboxylic acid, a hydroxy acid, an aldehyde, an ester, an alcohol, a cresol, a nitrile or a corresponding salt or derivative related thereto; and
a fermentation-derived product from biosynthesis of the carbon containing substance obtained from the waste stream of the non-biosynthetic process by the organism,
wherein the fermentation-derived product is selected from the group consisting of isopropanol, acetone, isoprene, ethanol, n-propanol, acetaldehyde, ethyl acetate, isobutylene and butadiene.

17. A process for producing isopropanol and/or acetone, said process comprising:
(a) introducing a carbon containing substance obtained from a waste stream of a non-biosynthetic process to a biosynthetic fermentation process, wherein the carbon containing substance is at least one of a carboxylic acid, a dicarboxylic acid, a hydroxy acid, an aldehyde, an ester, an alcohol, a cresol, a nitrile or a corresponding salt or derivative related thereto;
(b) adding to the biosynthetic fermentation process a Cupriavidus necator host of the H16 strain with at least a portion of the phaC1AB1 gene locus knocked out (ΔphaCAB) and genetically modified to comprise polynucleotides with at least 90% sequence identity to SEQ ID NO: 1, 3, 5, 7 and 9 or encode polypeptides with at least 90% sequence identity to SEQ ID NO:2, 4, 6, 8 and 10 which exhibit at least 75% of the activity of the corresponding mature, full-length, polypeptide of SEQ ID NO:2, 4, 6, 8 and 10, wherein the organism is capable of utilizing carbon in the one or more carbon containing substances;
(c) culturing the organism under conditions suitable for biosynthesis of the isopropanol and/or acetone; and
(d) biosynthesizing the isopropanol and/or acetone.

18. The method of claim 17 wherein the organism is genetically modified to:
   comprise polynucleotides with at least 95% sequence identity to SEQ ID NO: 1, 3, 5, 7 and 9 or encode polypeptides with at least 95% sequence identity to SEQ ID NO: 2, 4, 6, 8 and 10 which exhibit at least 75% of the activity of the corresponding mature, full-length, polypeptide of SEQ ID NO:2, 4, 6, 8 and 10.

* * * * *

SEQUENCE LISTING

```
<160> NUMBER OF SEQ ID NOS: 10

<210> SEQ ID NO 1
<211> LENGTH: 1185
<212> TYPE: DNA
<213> ORGANISM: C. necator

<400> SEQUENCE: 1
atgacgcgtg aagtggtagt ggtaagcggt gtccgtaccg cgatcgggac ctttggcggc      60
agcctgaagg atgtggcacc ggcggagctg ggcgcactgg tggtgcgcga ggcgctggcg     120
cgcgcgcagg tgtcgggcga cgatgtcggc cacgtggtat tcggcaacgt gatccagacc     180
gagccgcgcg acatgtatct gggccgcgtc gcggccgtca acggcggggt gacgatcaac     240
gcccccgcgc tgaccgtgaa ccgcctgtgc ggctcgggcc tgcaggccat tgtcagcgcc     300
gcgcagacca tcctgctggg cgataccgac gtcgccatcg gcggcggcgc ggaaagcatg     360
agccgcgcac cgtacctggc gccggcagcg cgctggggcg cacgcatggg cgacgccggc     420
ctggtcgaca tgatgctggg tgcgctgcac gatcccttcc atcgcatcca catgggcgtg     480
accgccgaga atgtcgccaa ggaatacgac atctcgcgcg cgcagcagga cgaggccgcg     540
ctggaatcgc accgccgcgc ttcggcagcg atcaaggccg gctacttcaa ggaccagatc     600
gtcccggtgg tgagcaaggg ccgcaagggc gacgtgacct tcgacaccga cgagcacgtg     660
cgccatgacg ccaccatcga cgacatgacc aagctcaggc cggtcttcgt caaggaaaac     720
ggcacggtca cggccggcaa tgcctcgggc ctgaacgacg ccgccgccgc ggtggtgatg     780
atggagcgcg ccgaagccga gcgccgcggc ctgaagccgc tggcccgcct ggtgtcgtac     840
ggccatgccg gcgtggaccc gaaggccatg ggcatcggcc cggtgccggc gacgaagatc     900
gcgctggagc gcgccgcct gcaggtgtcg gacctggacg tgatcgaagc caacgaagcc     960
tttgccgcac aggcgtgcgc cgtgaccaag gcgctcggtc tggacccggc caaggttaac    1020
ccgaacggct cgggcatctc gctgggccac ccgatcggcc ccaccggtgc cctgatcacg    1080
gtgaaggcgc tgcatgagct gaaccgcgtg cagggccgct acgcgctggt gacgatgtgc    1140
```

-continued atcggcggcg ggcagggcat tgccgccatc ttcgagcgta tctga          1185

<210> SEQ ID NO 2
<211> LENGTH: 394
<212> TYPE: PRT
<213> ORGANISM: C. necator

<400> SEQUENCE: 2

Met Thr Arg Glu Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
    130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Glu Arg Arg Gly Leu Lys
            260                 265                 270

Pro Leu Ala Arg Leu Val Ser Tyr Gly His Ala Gly Val Asp Pro Lys
        275                 280                 285

Ala Met Gly Ile Gly Pro Val Pro Ala Thr Lys Ile Ala Leu Glu Arg
    290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365

```
Arg Val Gln Gly Arg Tyr Ala Leu Val Thr Met Cys Ile Gly Gly Gly
    370                 375                 380
Gln Gly Ile Ala Ala Ile Phe Glu Arg Ile
385                 390
```

<210> SEQ ID NO 3
<211> LENGTH: 702
<212> TYPE: DNA
<213> ORGANISM: C. necator

<400> SEQUENCE: 3

```
atgaacaagg tctacgccag cgccgcagaa gcgcttgcag cgtcgtccg cgacggccag      60
acgatcgccg tgggcggttt cggcctgtgc ggcatccccg aggcgctgat tgccgcgctg     120
cgcgacagcg gcgccaagca gctgacctgt atctccaaca acgccggcgt cgatggcttc     180
ggcctgggcc tgctgctggc cacgcgccag atcagcaaga tgatctcgtc ctacgtgggc     240
gagaacaagg agttcgagcg ccagtacctg gcgggcgaac ttgagctgga attcaccccg     300
caaggcacgc tggccgagaa gctgcgcgcc ggcggctcgg gcatcccggc cttcttcacc     360
aagaccggtg tcggcaccat cgtcgccgaa ggcaaggaaa tccgcgaatt cgacggccag     420
cagtacgtga tggagcgttc gctgaccgcc gacgtggcgc tggtcaaggc atacaaggct     480
gacaaggccg gcaacctggt gttccgccgc accgcgcgca acttcaaccc gatgtgcgcc     540
atggcgggca aggtcaccat cgccgaggtc gagcatatcg tcgagaccgg cgagctggac     600
ccggatgaaa tccacctggc cggcatcttc gtgaagcgcc tggtgctgaa caccaccccc     660
gagaaacgca tcgagcagcg caccgtgcgc gcggccagct aa                        702
```

<210> SEQ ID NO 4
<211> LENGTH: 233
<212> TYPE: PRT
<213> ORGANISM: C. necator

<400> SEQUENCE: 4

```
Met Asn Lys Val Tyr Ala Ser Ala Ala Glu Ala Leu Ala Gly Val Val
1               5                   10                  15
Arg Asp Gly Gln Thr Ile Ala Val Gly Gly Phe Gly Leu Cys Gly Ile
                20                  25                  30
Pro Glu Ala Leu Ile Ala Ala Leu Arg Asp Ser Gly Ala Lys Gln Leu
            35                  40                  45
Thr Cys Ile Ser Asn Asn Ala Gly Val Asp Gly Phe Gly Leu Gly Leu
        50                  55                  60
Leu Leu Ala Thr Arg Gln Ile Ser Lys Met Ile Ser Ser Tyr Val Gly
65                  70                  75                  80
Glu Asn Lys Glu Phe Glu Arg Gln Tyr Leu Ala Gly Glu Leu Glu Leu
                85                  90                  95
Glu Phe Thr Pro Gln Gly Thr Leu Ala Glu Lys Leu Arg Ala Gly Gly
            100                 105                 110
Ser Gly Ile Pro Ala Phe Phe Thr Lys Thr Gly Val Gly Thr Ile Val
        115                 120                 125
Ala Glu Gly Lys Glu Ile Arg Glu Phe Asp Gly Gln Gln Tyr Val Met
    130                 135                 140
Glu Arg Ser Leu Thr Ala Asp Val Ala Leu Val Lys Ala Tyr Lys Ala
145                 150                 155                 160
Asp Lys Ala Gly Asn Leu Val Phe Arg Arg Thr Ala Arg Asn Phe Asn
                165                 170                 175
```

```
Pro Met Cys Ala Met Ala Gly Lys Val Thr Ile Ala Glu Val His
            180                 185                 190

Ile Val Glu Thr Gly Glu Leu Asp Pro Asp Glu Ile His Leu Ala Gly
        195                 200                 205

Ile Phe Val Lys Arg Leu Val Leu Asn Thr Thr Pro Glu Lys Arg Ile
    210                 215                 220

Glu Gln Arg Thr Val Arg Ala Ala Ser
225                 230
```

```
<210> SEQ ID NO 5
<211> LENGTH: 639
<212> TYPE: DNA
<213> ORGANISM: C. necator

<400> SEQUENCE: 5
atggcatgga cacgtgacga aatggccgcg cgcgccgcga ccgagctgca ggacggtttc    60
tacgtcaacc tgggcatcgg cctgccgacg ctggtggcca actgggtgcc cgaaggcatg   120
gaagtgtggc tgcagtccga gaacggactg ctgggcatcg cccgttcccc gaccgaggac   180
gaagtcgacg ccgacatgat caacgccggc aagcaaaccg tgacgacgct gccgggctcg   240
tcgatcttct cgtcggccga ctcgttcgcg atgatccgcg gcggccacat caacctggcg   300
atcctgggtg cgatgcaggt cagcgaaaag ggcgacctgg ccaactggat gatcccgggc   360
aagatggtca gggcatggg cggcgcgatg gacctggtcg ccggcgtcgg ccgagtggtg   420
gtgctgatgg aacacaccgc caagaagaag gatggcaccg aggacatcaa gatcctgaag   480
gactgcaacc tgccgctgac cggcgtgggc gtggtcaacc gcatcattac cgacctgggc   540
gtgatcgacg tgaccgacga aggcctgaag ctggtggaaa cggctccggg tgtcagccgc   600
gaggaaatcc aggccaagac tggcgctccg ctgctgtaa                          639
```

```
<210> SEQ ID NO 6
<211> LENGTH: 211
<212> TYPE: PRT
<213> ORGANISM: C. necator

<400> SEQUENCE: 6

Met Ala Trp Thr Arg Asp Glu Met Ala Ala Arg Ala Ala Thr Glu Leu
1               5                   10                  15

Gln Asp Gly Phe Tyr Val Asn Leu Gly Ile Gly Leu Pro Thr Leu Val
            20                  25                  30

Ala Asn Trp Val Pro Glu Gly Met Glu Val Trp Leu Gln Ser Glu Asn
        35                  40                  45

Gly Leu Leu Gly Ile Gly Pro Phe Pro Thr Glu Asp Glu Val Asp Ala
    50                  55                  60

Asp Met Ile Asn Ala Gly Lys Gln Thr Val Thr Thr Leu Pro Gly Ser
65                  70                  75                  80

Ser Ile Phe Ser Ser Ala Asp Ser Phe Ala Met Ile Arg Gly Gly His
                85                  90                  95

Ile Asn Leu Ala Ile Leu Gly Ala Met Gln Val Ser Glu Lys Gly Asp
            100                 105                 110

Leu Ala Asn Trp Met Ile Pro Gly Lys Met Val Lys Gly Met Gly Gly
        115                 120                 125

Ala Met Asp Leu Val Ala Gly Val Gly Arg Val Val Leu Met Glu
    130                 135                 140

Thr Ala Lys Lys Lys Asp Gly Thr Glu Asp Ile Lys Ile Leu Lys Asp
145                 150                 155                 160
```

Cys Asn Leu Pro Leu Thr Gly Val Gly Val Val Asn Arg Ile Ile Thr
              165                 170                 175

Asp Leu Gly Val Ile Asp Val Thr Asp Glu Gly Leu Lys Leu Val Glu
          180                 185                 190

Thr Ala Pro Gly Val Ser Arg Glu Glu Ile Gln Ala Lys Thr Gly Ala
      195                 200                 205

Pro Leu Leu
    210

<210> SEQ ID NO 7
<211> LENGTH: 735
<212> TYPE: DNA
<213> ORGANISM: Artificial sequence
<220> FEATURE:
<223> OTHER INFORMATION: Synthetic

<400> SEQUENCE: 7
atgctgaagg acgaagtcat caagcagatc tcgaccccgc tgacgagccc ggcgttcccg    60
cgcggcccgt acaagttcca caaccgcgaa tacttcaaca tcgtgtaccg caccgacatg   120
gacgcgctgc gcaaggtggt cccggagccg ctggaaatcg acgagccgct ggtccgcttc   180
gaaatcatgg cgatgcacga caccagcggc ctgggctgct acacggagag cggccaggcc   240
atcccggtgt cgttcaacgg cgtcaagggc gactacctgc atatgatgta cctggacaac   300
gaaccggcca tcgcggtggg ccgcgagctg agcgcctacc gaagaagct gggctacccg    360 aagctgttcg tggactcgga caccctggtc ggcacgctgg actacggcaa gctgcgcgtg   420
gccaccgcga cgatgggcta caagcacaag gccctggacg cgaacgaggc caaggaccag   480
atctgccgcc cgaactacat gctgaagatc atcccgaact acgacggctc gccgcgcatc   540
tgcgaactga tcaacgcgaa gatcaccgac gtcacggtcc acgaggcctg gaccggcccg   600
acgcgcctgc agctgttcga ccatgccatg gcgccgctga cgacctgcc ggtgaaggaa    660 atcgtgtcgt cgtcgcatat cctggcggac atcatcctgc gcgcgcagga ggtgatctac   720
gactacctga agtga                                                   735

<210> SEQ ID NO 8
<211> LENGTH: 244
<212> TYPE: PRT
<213> ORGANISM: Artificial sequence
<220> FEATURE:
<223> OTHER INFORMATION: Synthetic

<400> SEQUENCE: 8

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
            115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
            195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 9
<211> LENGTH: 1056
<212> TYPE: DNA
<213> ORGANISM: Artificial sequence
<220> FEATURE:
<223> OTHER INFORMATION: Synthetic

<400> SEQUENCE: 9

| | | | | | |
|---|---|---|---|---|---|
| atgaagggct | cgccatgct | gggcatcaac | aagctgggct | ggatcgaaaa | ggaacgcccg | 60 |
| gtcgccggct | cgtacgacgc | catcgtgcgc | ccgctggccg | tgtcgccgtg | caccagcgac | 120 |
| atccacacgg | tgttcgaggg | cgccctgggc | gaccgcaaga | acatgatcct | gggccatgag | 180 |
| gcggtgggcg | aggtggtcga | agtcggcagc | gaagtgaagg | acttcaagcc | gggcgaccgc | 240 |
| gtcatcgtgc | cgtgcaccac | gccggactgg | cgctcgctgg | aggtgcaggc | cggcttccag | 300 |
| cagcacagca | acggcatgct | ggcgggctgg | aagttctcga | acttcaagga | cggcgtcttc | 360 |
| ggcgaatact | ccatgtgaa | cgacgccgac | atgaacctgg | cgatcctgcc | gaaggacatg | 420 |
| ccgctggaga | cgccgtgat | gatcaccgac | atgatgacca | cgggcttcca | cggcgccgaa | 480 |
| ctggcggaca | tccagatggg | ctcgtcggtg | gtcgtgatcg | gcatcggcgc | cgtgggcctg | 540 |
| atgggcatcg | ccggcgcgaa | gctgcgcggc | gcgggccgca | tcatcggcgt | cggcagccgc | 600 |
| ccgatctgcg | tggaggccgc | gaagttctac | ggcgcgaccg | acatcctgaa | ctacaagaac | 660 |
| ggccacatcg | tcgaccaggt | gatgaagctg | accaacggca | agggcgtcga | ccgcgtgatc | 720 |
| atggccggcg | cggctcgga | aacgctgagc | caggcggtct | cgatggtgaa | gccgggcggc | 780 |
| atcatcagca | acatcaacta | ccacggctcg | ggcgacgccc | tgctgatccc | gcgcgtggag | 840 |
| tggggctgcg | gcatggcgca | taagaccatc | aaggggcggcc | tgtgccaggg | cggccgcctg | 900 |
| cgcgccgaaa | tgctgcgcga | catggtcgtg | tacaaccgcg | tggacctgtc | gaagctggtg | 960 |
| acccacgtgt | accatggctt | cgaccacatc | gaggaagccc | tgctgctgat | gaaggacaag | 1020 |
| ccgaaggacc | tgatcaaggc | ggtcgtgatc | ctgtga | | | 1056 |

<210> SEQ ID NO 10
<211> LENGTH: 351
<212> TYPE: PRT
<213> ORGANISM: Artificial sequence
<220> FEATURE:

<223> OTHER INFORMATION: Synthetic

<400> SEQUENCE: 10

```
Met Lys Gly Phe Ala Met Leu Gly Ile Asn Lys Leu Gly Trp Ile Glu
1               5                   10                  15
Lys Glu Arg Pro Val Ala Gly Ser Tyr Asp Ala Ile Val Arg Pro Leu
            20                  25                  30
Ala Val Ser Pro Cys Thr Ser Asp Ile His Thr Val Phe Glu Gly Ala
        35                  40                  45
Leu Gly Asp Arg Lys Asn Met Ile Leu Gly His Glu Ala Val Gly Glu
    50                  55                  60
Val Val Glu Val Gly Ser Glu Val Lys Asp Phe Lys Pro Gly Asp Arg
65                  70                  75                  80
Val Ile Val Pro Cys Thr Thr Pro Asp Trp Arg Ser Leu Glu Val Gln
                85                  90                  95
Ala Gly Phe Gln Gln His Ser Asn Gly Met Leu Ala Gly Trp Lys Phe
            100                 105                 110
Ser Asn Phe Lys Asp Gly Val Phe Gly Glu Tyr Phe His Val Asn Asp
        115                 120                 125
Ala Asp Met Asn Leu Ala Ile Leu Pro Lys Asp Met Pro Leu Glu Asn
    130                 135                 140
Ala Val Met Ile Thr Asp Met Met Thr Thr Gly Phe His Gly Ala Glu
145                 150                 155                 160
Leu Ala Asp Ile Gln Met Gly Ser Ser Val Val Ile Gly Ile Gly
                165                 170                 175
Ala Val Gly Leu Met Gly Ile Ala Gly Ala Lys Leu Arg Gly Ala Gly
            180                 185                 190
Arg Ile Ile Gly Val Gly Ser Arg Pro Ile Cys Val Glu Ala Ala Lys
            195                 200                 205
Phe Tyr Gly Ala Thr Asp Ile Leu Asn Tyr Lys Asn Gly His Ile Val
    210                 215                 220
Asp Gln Val Met Lys Leu Thr Asn Gly Lys Gly Val Asp Arg Val Ile
225                 230                 235                 240
Met Ala Gly Gly Gly Ser Glu Thr Leu Ser Gln Ala Val Ser Met Val
                245                 250                 255
Lys Pro Gly Gly Ile Ile Ser Asn Ile Asn Tyr His Gly Ser Gly Asp
            260                 265                 270
Ala Leu Leu Ile Pro Arg Val Glu Trp Gly Cys Gly Met Ala His Lys
        275                 280                 285
Thr Ile Lys Gly Gly Leu Cys Pro Gly Gly Arg Leu Arg Ala Glu Met
    290                 295                 300
Leu Arg Asp Met Val Val Tyr Asn Arg Val Asp Leu Ser Lys Leu Val
305                 310                 315                 320
Thr His Val Tyr His Gly Phe Asp His Ile Glu Glu Ala Leu Leu Leu
                325                 330                 335
Met Lys Asp Lys Pro Lys Asp Leu Ile Lys Ala Val Val Ile Leu
            340                 345                 350
```